United States Patent
Sinn et al.

(10) Patent No.: US 6,720,304 B1
(45) Date of Patent: Apr. 13, 2004

(54) CONJUGATE COMPRISING A FOLIC ACID ANTAGONIST AND A CARRIER

(75) Inventors: Hannsjörg Sinn, Wiesloch (DE); Hans-Herman Schrenk, Zeiskam (DE); Wolfgang Maier-Borst, Dossenheim (DE); Eva Frei, Heidelberg (DE); Gerd Stehle, Heidelberg (DE)

(73) Assignee: Deutsches Krebsforschungszentrum Stiftung Des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/423,710

(22) PCT Filed: May 8, 1998

(86) PCT No.: PCT/EP98/02701

§ 371 (c)(1),
(2), (4) Date: Jul. 13, 2000

(87) PCT Pub. No.: WO98/51349

PCT Pub. Date: Nov. 19, 1998

(30) Foreign Application Priority Data

May 9, 1997 (EP) .............................. 97107657

(51) Int. Cl.[7] ........................ A61K 47/48; A61K 38/38; C07D 475/04; C07D 475/08
(52) U.S. Cl. ............................. 514/2; 514/12; 514/249; 514/564; 530/324; 530/350; 530/810; 530/816; 424/9.1; 544/258; 544/260
(58) Field of Search ............................... 514/2, 12, 249, 514/564, 14, 772.3, 772.4; 530/324, 350, 810, 816, 325, 326; 424/9.1; 544/258, 260

(56) References Cited

FOREIGN PATENT DOCUMENTS

| DE | 44 33 890 A1 | * | 3/1996 |
|---|---|---|---|
| EP | 0 251 455 A | | 1/1988 |
| WO | WO 85/00812 A | | 2/1985 |
| WO | WO 93/15751 A | | 8/1993 |

OTHER PUBLICATIONS

Schulz et al., REactions of polymer analogs with methotrexate, Z. Chem. (1987) 27(12):437–438.*

Zalipsky et al., Poly(Ethylene Glycol) Chemistry: Biotechnical and Biomedical Applications, J. Milton Harris, ed., Plenum Press, NY (1992) pp. 347–370.*

Frei et al., 1997, "Cellular uptake and method of methotrexate bound to albumin differs from that of free methotrexate," *Proceedings of the American Association of Cancer Research Annual Meeting*, Eighty–Eighth Annual Meeting of the American Association for Cancer Research, San Siego CA. Apr. 12–16, 1997, vol. 38, p. 432.

Jackman et al., 1993, "Gamma–linked dipeptide analgoues of 2–desamino–2–methyl–N10–propargyl–5,8–dideazafolate as antitumour agents," *Adv. Exp. Med. Biol.* 338: 579–584.

Lee et al., 1974, "Folic acid antagonists. Methotrexate analogs containing spurious amino acids. Dichlorohomofolic acid," *J. Med. Chem.* 17(3):326–330.

* cited by examiner

Primary Examiner—Christopher S. F. Low
Assistant Examiner—Chih-Min Kam

(57) ABSTRACT

The invention relates to conjugates comprising a D-enantiomer of a folic acid antagonist and a carrier. Furthermore, the invention relates to the production of such conjugates as well as their use.

4 Claims, No Drawings

CONJUGATE COMPRISING A FOLIC ACID ANTAGONIST AND A CARRIER

This is a national phase filing of the Applicaton Ser. No. PCT/EP98/02701, which was filed with the Patent Corporation Treaty on May 8, 1998, and is entitled to priority of the German Patent Application 97107657.5, filed May 9, 1997.

I. FIELD OF THE INVENTION

The invention relates to a conjugate comprising a folic acid antagonist and a carrier, a method for the production of such a conjugate as well as it's use.

II. BACKGROUND OF THE INVENTION

Folic acid is a compound present in nature which is important in cells for methyl group transfer and thus for the growth of cells. Folic acid has the following formula:

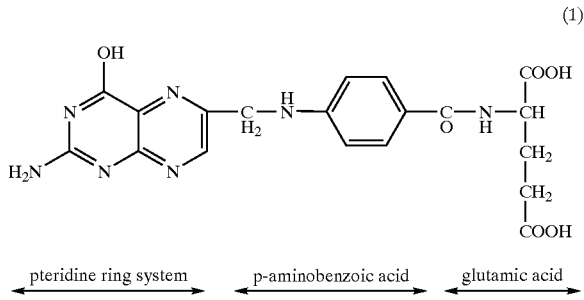

(1)

The CH group of the glutamic acid represents an asymmetric C atom. Therefore, folic acid exists in two enantiomeric forms, namely as D- and L-enantiomers.

However, only the L-enantiomer from these enantiomeric forms is found in cells, so that only this form, but not the D-enantiomer, is responsible for the action of folic acid. The reason for this is that folic acid is taken up in cells by the foliate receptor, which however only takes up the L-enantiomer, but not the D-enantiomer, of folic acid.

Folic acid antagonists are compounds which are derivative from folic acid but counteract the latter at its target area, namely in cells. Therefore, folic acid antagonists are present as L-enantiomers but not as D-enantiomers. Examples of folic acid antagonists are aminomopterin and amethopterin which is also designated as methotrexate.

Methotrexate, i.e., the L-enantiomer of amethopterin, is frequently employed for the treatment of tumors and inflammations. However, major side-effects have been demonstrated for this because methotrexate is also taken up by healthy tissue and is toxic for it DE-A-41 22210.5 alone describes conjugates of methotrexate and albumin which are taken up better by tumors than by healthy tissue and are thus less toxic. Nevertheless, a great need exists for agents which have even weaker side-effects.

Therefore, the object of the present invention is to provide an agent for the treatment of diseased tissues, especially tumors, which has the weakest side-effects.

III. SUMMARY OF THE INVENTION

The invention relates to conjugates comprising a D-enantiomer of a folic acid antagonist and a carrier. Furthermore, the invention relates to the production of such conjugates as well as their use.

IV. DETAILED DESCRIPTION OF THE INVENTION

The object of the present invention is to provide an agent for the treatment of diseased tissues, especially tumors, which has the weakest side-effects. This is attained according to the invention by the subject matter of the claims.

Thus, subject matter of the present invention is a conjugate which comprises the D-enantiomer of a folic acid antagonist and a carrier.

The present invention is based on the applicant's insights that the D-enantiomer of a folic acid antagonist in a conjugate having a carrier is preferably taken up by disease tissues, especially tumor cells, and displays an effect against the disease in them. Furthermore, the applicant recognized that the D-enantiomer of a folic acid antagonist alone, i.e., not present in a conjugate according to the invention, has no side-effects on healthy tissue.

The term 'conjugate' indicates that the folic acid antagonist and the carrier are covalently bound, for example through amide and/or ester bonds and/or via a linker.

The term 'D-enantiomer of a folic acid antagonist' comprises compounds of any sort which are derived from folic acid, function as an antagonist of folic acid and are present as a D-enantiomer. As components, the D-enantiomer of a folic acid antagonist comprises pteridine, especially pterine, p-aminobenzoic acid and a D-amino acid, especially D-glutamic acid, which are chemically altered, i.e., modified, with respect to the components in folic acid. Such alterations are, for example, substitutions such as the substitution of H atoms by $C_1$–$C_4$ allyl groups, especially methyl group, halogen atoms such as F, Cl, Br, I, OH— and $NH_2$-groups, the substitution of OR-groups by the above alkyl groups, $NH_2$-groups, H— and halogen atoms as well as the substitution of $NH_2$-groups by the above alkyl groups, OH— groups, H— and halogen atoms. Furthermore, one or both of the acid groups of the glutamic acid can be present as an acid derivative, for example, as an ester or amide. One or more of the above alterations can be present in a folic acid antagonist used according to the invention.

Preferably, the folic acid antagonists D-amethopterine (designated in the following as D-methotrexate) and D-e,t-FMTX (a metetroxate analogue in which the glutamic acid (Glu) is replaced by D-erythro, threo-4-flouro-Glu).

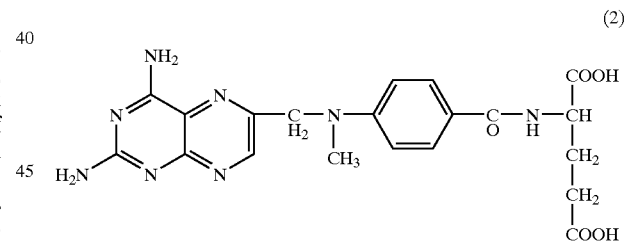

(2)

D-aminoterine

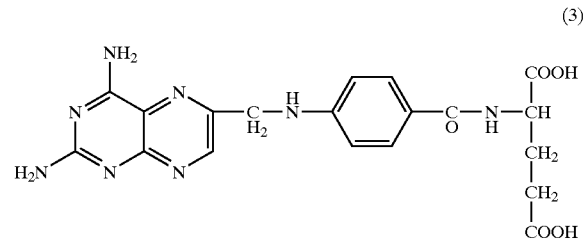

(3)

One or more of the folic aid antagonists can be present in the conjugate according to the invention. If several are present, then these can be the same or different from each other.

The term 'carrier' comprises compounds of any sort which are suitable for accumulating the conjugate in a diseased tissue, for example, tumor or inflammation focus. Examples of such carriers are proteins which are not considered as foreign to the body and polyether.

The proteins are preferably present in native form. In the native form, the proteins do not have ay inter- and/or intramolecular cross-linking. Favorably, the proteins have a molecular weight of up to 100,000 Dalton, especially 30,000 to 100,000 Dalton.

Furthermore, its favorable when the proteins are human proteins. Examples of the proteins are albumin, fibronigen, transferrin, immunoglobulins and lipoproteins, human albumin being preferred. Fragments of the above proteins can also be used. Furthermore, the sequence of the proteins and/or fragments thereof can have alterations of one or more amino acids in comparison with the known sequence of the proteins and/or fragments thereof.

Examples of the polyethers are polyethylene glycols, especially those with a molecular weight from 100 to 20,000 Dalton. Preferably, the polyethylene glycols are esterified or etherified on the terminal hydroxyl group with a $C_1$–$C_{12}$ alyl group, especially with a methyl group.

A conjugate according to the invention can have one or more, especially two, of the above carriers. If several carriers are present, these can be the same or different from each other. If several polyethers are present, they will favorably be selected in such a manner that the molecular weight of all polyethers amounts to about 20,000 Daltons or more.

In the conjugate according to the invention the folic acid antagonist can be directly covalently bound with the carrier or bound via a linker, i.e., a linker is present between carrier and folic acid antagonist. All compounds are suitable as a linker which can bond the folic acid antagonist and carrier.

Preferably, the linker can be cleaved in a cell. The term 'cell' comprises individual cells and cell aggregates. Examples of the former are endogenous cells not present in an aggregate. Cell aggregates comprise tissues, organs and tumors.

A linker of the above type is known to the skilled person. He also knows factors, for example, enzymes which cause the cleavage of certain chemical bonds in cells. Thus, he is able to construct linkers which can be cleaved in a cell. Particularly preferred, such a linker comprises an azo group. It is particularly favorable when the linker has the following structure:

-Y-R-N- wherein

R is an organic group, preferably an aromatic, and particularly preferably phenylene or a derivative thereof, and Y is selected from a group of C(O), S(O)$_2$, P(O)OH and As (O) OH.

The above structure of a preferred linker corresponds to that which the linker has in a conjugate according to the invention. Furthermore, the structure comprises, at least when R is phenylene or a derivative thereof, an active compound which is particularly suitable for the therapy of tumoral, inflammatory and autoimmune diseases. The compound can display its full effect after the cleavage of the linker and the optional degradation of the protein still bound to the linker.

Conjugates according to the invention can be produced by covalently bonding the folic acid antagonist with the carrier and optionally the linker. Suitable methods as well as the necessary materials for this are known to the skilled person.

When the folic acid antagonist has at least one carboxyl group, for example those present through the glutamic acid, the conjugates can be produced by converting the folic acid antagonist with carboiimide and hydroxysuccinimide into reactive succinimidyl esters and reacting these with the carrier. In the case of conjugates with folic acid antagonists, the production of the succinimidyl esters can occur jointly or separately.

The conversion of the folic acid antagonist with carboiimide and hydroxysuccinimide occurs in a polar aprotic solvent, preferably dimethylformamide (DMF). The molratio of folic acid antagonist:carbodiimide:hydroxysuccinimide amounts to about 1:14:10. The succinimidyl ester formed is then reacted with the carrier such as albumin in an aqueous buffer solution, preferably NaHCO$_3$. The carrier concentration amounts to about 10 to 70 mg/ml. The carboxyl group activated in this manner can then react with OH- and NH-groups of the carrier thereby forming acid amide or acid ester bonds, conjugates according to the invention being obtained. The conjugates can be purified several times, for example by ultrafiltration, and can be finally sterile filtered whereby they are ready for application.

Conjugates according to the invention are distinguished by the fact that they remain in the circulation of the patient over a long time. Furthermore, the accumulate in diseased tissues, especially tumors and inflammation foci. Moreover, they am distinguished by the fact that they have even weaker side-effects than conjugates with L-folic acid antagonists as known from DE-A-41 22 210.5, their action against diseased tissue, especially tumors and inflammation foci, being maintained.

Therefore, conjugates according to the invention are perfectly suited for the treatment of tumors such as hermatological and solid tumors, inflammations, for example diseases of the rheumatic form such as chronic polyartritis or psoriasis, and autoimmune diseases.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

V. EXAMPLES

A. Example 1

Production of a Conjugate According to the Invention of D-methotrexate and Human Serum Albumin D-methotrexate (D-MTX) was dissolved in DMF at a concentration of 20 mg/mL 1.5 times the molar amount of di-cyclohexylcarbodiimide and about 10 times the molar amount of hydroxysuccinimide were added to the clear yellow solution. After a reaction time of about 12 hours, the conversion into the succinimidyl ester (DMTX-HSIE) is concluded and is recognizable by the precipitated amount of di-cyclohexylurea (DCU). The analytic control of the reaction was carried out by means of TLC.

plates: silica gel 60 with fluorescene indicator, running agent, ethyl acetate/MeOH: 75/25,

| R$_f$ values: | D-MTX | 0.0 |
|---|---|---|
| | D-MTX-HSIE | 0.35–0.38 |

The clear yellow solution of D-MrX-HSIE in DMF was added slowly with constant stirring to the protein solution (50–70 mg human serum albumin 0.17 M NaHCO$_3$, pH 8.5), a cloud consisting of non-reacted di-cyclohexylcarbodiimide and DCU still dissolved in DMF forming after some time. After a reaction time of at least 30 minutes, the cloud was separated through a sterile filter (0.22 μm) and the DMF was separated by ultrafiltration with appropriate membrane filter (YM30; Amicon).

The purity control was conducted by means of HPLC:

| | |
|---|---|
| pre-column: | 50 × 4 mm Zorbax Diol |
| columns: | 1$^{st}$ Zorbax GF 450 |
| | 2$^{nd}$ Zorbax GF 250 |
| running agent: | 0.2 M phosphate buffer, pH 7.4 |
| flow: | 1.0 ml/min |
| pressure: | about 65 bar |

A conjugate according the invention of D-methotrexate and human serum albumin was obtained.

B. Example 2

Comparison Between the Toxicity of a Conjugate According to the Invention of D-metholate and Human Serum Albumin and a Conjugate of Metetroxate and Human Serum Albumin For this experiment, the conjugate according to the invention of D-methotrexate and human serum albumin (D-MTX-HSA) from Example 1 was used. Furthermore, the conjugate of methotrexate and human serum albumin (MTX-HSA) known from DE-A-.41 22 210.5 was employed.

Each of 5 healthy Sprague-Dawley rats received D-MTX-HSA or MTX-HSA. In each case, 4 mg conjugate (based on the amount of MTX or D-MTX of the conjugate) per kg body weight was injected at a 2-day interval.

The results are presented in TABLE 1.

TABLE 1

The Results of the Determination of the Toxicity of MTX-HSA and D-MX-HSA After the 3$^{rd}$ Day

| | dose/kg | MI | DI | SC | WL | death |
|---|---|---|---|---|---|---|
| MTX-HSA | 2 × 4 mg | 5 | 5 | 5 | 5 | 5 |
| D-MTX-HSA | 2 × 4 mg | 0 | 0 | 0 | 0 | 0 |

Abbreviations:
MI: muscus membrane inflammation;
DI: diarrhea;
SC: shaggy coat;
WL: weight loss.

As emerges from TABLE 1, the rats already suffered from strong side-effects from the 3$^{rd}$ day with administration of MTX-HSA. On the 4$^{th}$ day, 2 rats were found dead in their cage. The other 3 rats had to be euthanized because they suffered from very strong side-effects. In contrast to this, no rat which was treated with the conjugate D-MTX-HSA according to the invention had side-effects.

Thus, conjugates according to the invention have weak side-effects.

C. Example 3

Tumor Therapy with a Conjugate According to the Invention of D-methotrexate and Human Serum Albumin in Comparison with a Conjugate of Methotrexate and Human Serum Albumin For this experiment, the conjugates given in Example 2 were used. Walker-256 carcinosarcoma-carrying rates were employed as experimental animals. The beginning of therapy was on the 6$^{th}$ day after tumor transplantation with tumor volumes of between 1,000 and 2,500 mm$^3$ (tumor diameter 1×1 to 1×2 cm). Five rats received MTX-HSA (3 injections at 2-day intervals with a dose of 2 mg MTX-HSA (based on the amount of MTX) per kg of body weight). The conjugate according to the invention D-MTX-HSA was administered with the double dose according to the above protocol. With this dose, considerable side-effects already appeared with MTX-HSA, however, not with conjugate D-MTX-HSA according to the invention (compare Example 2).

The results are presented in TABLE 2.

TABLE 2

Results of the Tumor Therapy with the Conjugate MTX-HSA and the Conjugate According to the Invention D-MTX-HSA

| | dose/kg | remission | relapse | SE | death |
|---|---|---|---|---|---|
| MTX-HSA | 3 × 2 mg | 3 | 2 | 3 | 2 |
| D-MTX-HSA | 3 × 4 mg | 5 | 0 | 0 | 0 |

Abbreviations:
SE: side-effects;
death: death by tumor relapse.

The results in TABLE 2 show that the tumor regressed in 3 rats (remission) in the MTX-HSA group. In this group, 2 rats suffered a relapse and had to be euthanized. In 3 rats, side-effects appeared. As opposed to this, it was shown that in rats which were treated with the conjugate D-MTX-HSA according to the invention, all animals were cured of the tumor and no side-effects were observable thereby although the double dose was used in comparison with MTX-HSA.

Thus, conjugates according to the invention have the weakest side-effects, so that an excellent tumor therapy can be attained with these conjugates.

All references cited within the body of the instant specification are hereby incorporated by reference in their entirety.

What is claimed is:

1. A conjugate comprising a D-enantiomer of a folic acid antagonist and a carrier, wherein said carrier is serum albumin and said folic acid antagonist is D-methotrexate or D-aminopterine.

2. The conjugate of claim 1, wherein a linker is present between said folic acid antagonist and said carrier, wherein said linker has the following formula:

-Y-R-N= wherein

R is phenylene, and Y is selected from a group of C(O), S(O)$_2$, P(O)OH and As (O) OH.

3. The conjugate of claim 2, wherein said linker can be cleaved in a cell.

4. A method for the production of the conjugate according to claim 1, comprising subjecting a D-enantiomer of a folic acid antagonist, a carrier and optionally a linker to conditions that they covalently bind to each other.

* * * * *